(12) United States Patent
Murata et al.

(10) Patent No.: US 6,620,817 B1
(45) Date of Patent: Sep. 16, 2003

(54) [5-CHLORO-6-PHENYL-2-(4-TRIFLUOROMETHYLPHENYL)-4-PYRIMIDINYLAMINO]ACETAMIDE DERIVATIVES, PROCESS FOR PRODUCING THE SAME, MEDICINAL COMPOSITIONS CONTAINING THE SAME AND INTERMEDIATE OF THESE COMPOUNDS

(75) Inventors: Teruya Murata, Izumiotsu (JP); Kazunori Ohno, Ikoma (JP); Masayasu Tanaka, Sakai (JP); Mari Itoh, Suita (JP)

(73) Assignee: Dainippon Pharmaceutical Co., Ltd., Osaka-Fu (JP)

( * ) Notice: Subject to any disclaimer, the term of this patent is extended or adjusted under 35 U.S.C. 154(b) by 46 days.

(21) Appl. No.: 10/130,151

(22) PCT Filed: Nov. 9, 2000

(86) PCT No.: PCT/JP00/07854

§ 371 (c)(1), (2), (4) Date: May 13, 2002

(87) PCT Pub. No.: WO01/36392

PCT Pub. Date: May 25, 2001

(30) Foreign Application Priority Data

Nov. 17, 1999 (JP) .......................................... 11-326290

(51) Int. Cl.[7] .................... C07D 239/42; A61K 31/505
(52) U.S. Cl. ...................................... 514/256; 544/329
(58) Field of Search ............................ 544/329; 514/256

(56) References Cited

U.S. PATENT DOCUMENTS 5,972,946 A    10/1999    Murata et al. .............. 514/256

FOREIGN PATENT DOCUMENTS

| EP | 826673 | 3/1998 |
|---|---|---|
| JP | 10-130150 | 5/1998 |
| WO | 98/09960 | 3/1998 |

*Primary Examiner*—John M. Ford
(74) *Attorney, Agent, or Firm*—Wenderoth, Lind & Ponack, L.L.P.

(57) ABSTRACT

A [5-chloro-6-phenyl-2-(4-trifluoromethylphenyl)-4-pyrimidinyl-amino]acetamide derivative of the formula (I):

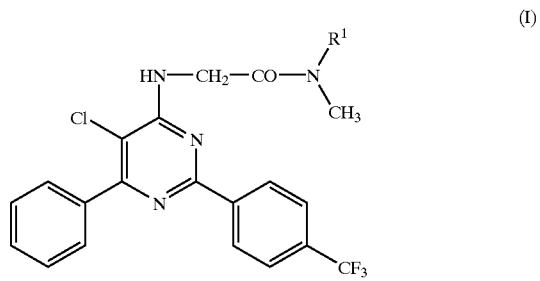

wherein $R^1$ is a methyl group or a cyclopropyl group, and a pharmaceutical composition containing the same. Said compounds exhibit a potent anti-rheumatoid activity and show low toxicity, and hence, they are useful as an agent for prophylaxis or treatment of immuno inflammatory diseases such as rheumatoid diseases (e.g., rheumatoid arthritis, Behcet disease, ankylosing spondylitis, etc.) and autoimmune diseases (e.g., multiple sclerosis, systemic lupus erythematosus, Sjögren syndrome, etc.).

11 Claims, No Drawings

[5-CHLORO-6-PHENYL-2-(4-TRIFLUOROMETHYLPHENYL)-4-PYRIMIDINYLAMINO]ACETAMIDE DERIVATIVES, PROCESS FOR PRODUCING THE SAME, MEDICINAL COMPOSITIONS CONTAINING THE SAME AND INTERMEDIATE OF THESE COMPOUNDS

This application is a 371 of PCT/JP00/07854, filed Nov. 9, 2000.

TECHNICAL FIELD

The present invention relates to a novel [5-chloro-6-phenyl-2-(4-trifluoromethylphenyl)-4-pyrimidinylamino] acetamide derivative being useful as an agent in the treatment of immuno inflammatory diseases, a process for preparing the same, a pharmaceutical composition containing the same, and an intermediate for preparing said acetamide derivative.

BACKGROUND ART

WO-96/32383 and JP-A-10-130150 disclose that the acetamide derivative of the following formula selectively acts on benzodiazepine $\omega_3$ receptors, and exhibits anti-anxiety activity and anti-rheumatoid activity, and is useful in the treatment of anxiety-related diseases and immune diseases.

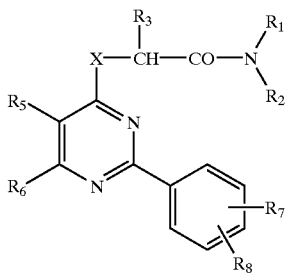

wherein X is —O— or —NR$_4$—,

R$_1$ is a hydrogen atom, a lower alkyl group, a lower alkenyl group or a cyclolalkyl-lower alkyl group, R$_2$ is a lower alkyl group, a cycloalkyl group, a substituted or unsubstituted phenyl group, a substituted or unsubstituted phenyl-lower alkyl group, etc., R$_3$ is a hydrogen atom, a lower alkyl group or a hydroxy-lower alkyl group, R$_4$ is a hydrogen atom, a lower alkyl group, etc., R$_5$ is a hydrogen atom, a lower alkyl group, a lower alkenyl group, a hydroxy-lower alkyl group, a substituted or unsubstituted benzyloxy-lower alkyl group, an acyloxy-lower alkyl group, a lower alkoxy-lower alkyl group, a trifluoromethyl group, a halogen atom, an amino group, a mono- or di-lower alkylamino group, an acylamino group, an amino-lower alkyl group, a nitro group, a carbamoyl group, a mono- or di-lower alkyl-carbamoyl group, a carboxyl group, a protected carboxyl group, a carboxy-lower alkyl group or a protected carboxy-lower alkyl group, R$_6$ is a hydrogen atom, a lower alkyl group, a trifluoromethyl group, or a substituted or unsubstituted phenyl group, or R$_5$ and R$_6$ may optionally combine to form —(CH$_2$)$_n$— (n is 3, 4, 5 or 6), R$_7$ is a hydrogen atom, a halogen atom, a lower alkyl group, a lower alkoxy group, a trifluoromethyl group, a hydroxy group, an amino group, a mono- or di-lower alkylamino group, a cyano group or a nitro group, R$_8$ is a hydrogen atom, a halogen atom, a lower alkyl group or a lower alkoxy group.

The above WO 96/32383 discloses as a compound having a 4-trifluoromethylphenyl group at the 2-position of the pyrimidine ring, and exhibiting anti-rheumatoid activity the compound of the following formula (A) (the compound of Example 6 of said publication).

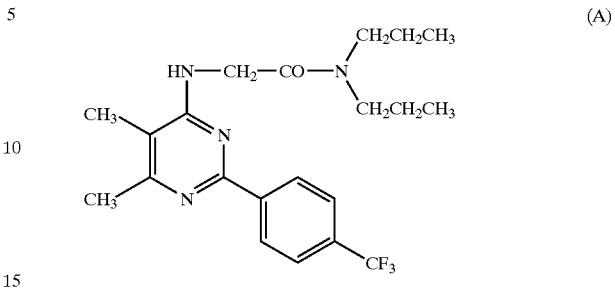

In addition, the above JP-A-10-130150 discloses, in addition to the compound of the above formula (A), as a compound having a 4-trifluoromethylphenyl group at the 2-position of the pyrimidine ring and exhibiting anti-rheumatoid activity the compound of the following formula (B) (the compound of Example 206 of said publication).

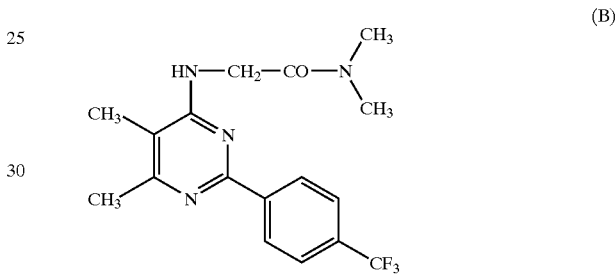

The compounds of the present invention of the formula (I) as mentioned below are conceptually included within the scope of the claims of said WO 96/32383, but said publication never concretely disclose the present compound. Then, as compared the structures of the compounds of the formulae (A) and (B) with that of the compound of the present invention as mentioned below, the former compounds have a 4-trifluoromethyl group at the 2-position of the pyrimidine ring but both the 5-position and the 6-position of the pyrimidine ring are methyl groups, and hence, they are structurally quite different from the latter compound (the compound of the present invention) in which the 5-position of the pyrimidine ring is substituted by a chlorine atom, and the 6-position thereof is a phenyl group.

WO 98/09960 discloses that a 2,4-disubstituted pyrimidine derivative of the following formula selectively acts on benzodiazepine 6)3 receptors like the compound of the above WO 96/32383.

wherein A is a heteroaryl group, etc., and the definitions for the other substituents are omitted, but either one of A and R$_2$ should be a heteroaryl group.

The compound of the present invention of the following formula (I) is apparently distinguished from the compound of the above formula in which at least one of the substituent (A) at the 2-position of the pyrimidine ring and $R_2$ is a heteroaryl group.

Immuno inflammatory diseases such as rheumatoid arthritis (hereinafter, occasionally referred to as rheumatism), Sjögren syndrome, Behcet disease, ankylosing spondylitis, etc. are differentiated in terms of being systemic crisis or being local crisis at a specific organ, but all of these diseases are intractable and cryptogenic diseases. Therefore, it is a present situation that the treatment of these diseases should be relied on non-specific anti-inflammatory therapy or immunosuppressive therapy. For example, non-steroid anti-inflammatory agents or steroidal agents have been used in the treatment of rheumatism so far. However, since it was recently found that immune-response abnormality is participated in the rheumatism, an immunosuppressive agent (e.g., methotrexate, mizoribine, etc.) or an immuno modulating agent (e.g., sulfasalazine, D-penicillamine, oral gold agents, etc.) has been positively used in the treatment of rheumatism. However, such drugs have serious side effects, respectively, and it is therapeutically very important to monitor the side effects in its course of treatment after the administration of these drugs. In addition, many of immuno modulating agents have a problem, that is, when they are continuously administered, the pharmacological effects thereof become weak or even disappear, which is a clinically very serious problem. Under the above-mentioned circumstances, it has been strongly desired to develop a therapeutic agent for immuno inflammatory diseases or an immuno modulating agent, with a high efficiency and a high safety.

The present inventors have intensively studied and tried on various pharmaceutical activities of the compounds selectively acting on benzodiazepine $\omega_3$ receptors, and during the process thereof, they have found the compounds exhibiting effects on immuno inflammatory diseases such as anti-rheumatoid activity, etc., and filed a patent application (the above WO 96/32383 and JP-A-10-130150). In the above publications, there is disclosed a compound having a 4-trifluromethyl group as the substituent on the phenyl group attached to the 2-position of the pyrimidine ring. For example, the compound of the above formula (A) disclosed in WO 96/32383 exhibits a rather potent anti-rheumatoid activity, but the efficacy thereof is not sufficient enough. In addition, JP-A-10-130150 discloses the compound of the above formula (B) exhibiting a more potent anti-rheumatoid activity, but by the research thereafter, it was found that the compound of the formula (B) has a much influence on liver and kidney, and this compound is not suitable as a medicament in terms of the safety.

DISCLOSURE OF INVENTION

The present inventors have intensively studied in order to obtain a [2-(4-trifluoromethylphenyl)-4-pyrimidinylamino] acetamide derivative having an anti-rheumatoid activity as potent as the compound of the above formula (B) and a high safety, and being useful as an agent for treatment or prophylaxis of immuno inflammatory diseases, and have found that a compound having a chloro substituent at the 5-position and a phenyl substituent at the 6-position of pyrimidine ring, i.e., a specific [5-chloro-6-phenyl-2-(4-trifluoromethyl-phenyl)-4-pyrimidinylamino]acetamide derivative of the formula (I) as shown below (hereinafter, occasionally referred to as the present compound) has unexpectedly a potent anti-rheumatoid activity but hardly has an influence on liver, etc., and finally have accomplished the present invention.

An object of the present invention is to provide a [5-chloro-6-phenyl-2-(4-trifluoromethylphenyl)-4-pyrimidinylamino]acetamide derivative having a potent anti-rheumatoid activity and a high safety, and being useful in the prophylaxis or treatment of immuno inflammatory diseases. Another object of the present invention is to provide a process for preparing said compound. Still further object of the present invention is to provide a pharmaceutical composition containing said compound. Further object of the present invention is to provide an intermediate for preparing said compound. These and other objects and advantages of the present invention are obvious to any person skilled in the art from the following disclosure.

The present invention provides a [5-chloro-6-phenyl-2-(4-trifluoromethylphenyl)-4-pyrimidinylamino]acetamide derivative of the formula (1):

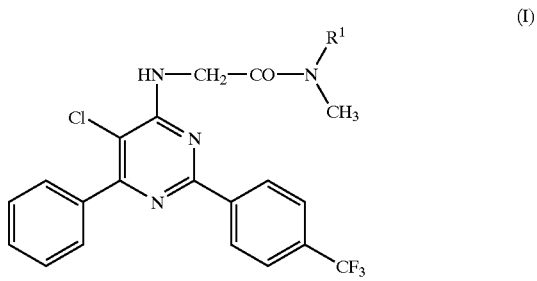

(I)

wherein $R^1$ is a methyl group or a cyclopropyl group, a process for preparing the same, and a pharmaceutical composition containing the same, and also provides an intermediate of the formula (II):

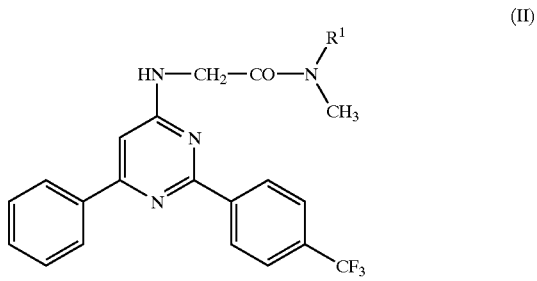

(II)

wherein $R^1$ is a methyl group or a cyclopropyl group.

The compounds of the formula (I) and the formula (II) may exist in the form of a hydrate and/or a solvate, and the present invention also includes these hydrates and/or solvates as well.

The compounds within the scope of the present invention are the following two compounds.

(1) 2-[5-chloro-6-phenyl-2-(4-trifluoromethylphenyl)-4-pyrimidinyl-amino]-N,N-dimethylacetamide:

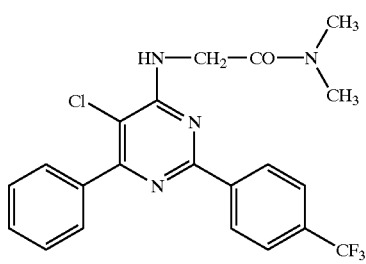

(2) 2-[5-chloro-6-phenyl-2-(4-trifluoromethylphenyl)-4-pyrimidinyl-amino]-N-cyclopropyl-N-methylacetamide:

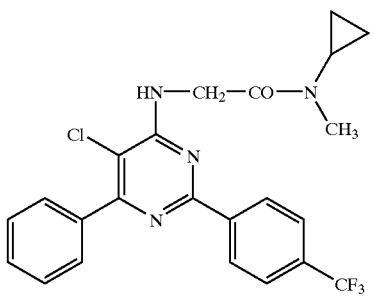

Among these two compounds, the compound (2) {2-[5-chloro-6-phenyl-2-(4-trifluoromethylphenyl)-4-pyrimidinylamino]-N-cyclopropyl-N-methylacetamide} is more preferable.

The compound of the present invention may be prepared by the following process.

The compound of the formula (I) may be prepared by chlorination of a compound of the following formula (II):

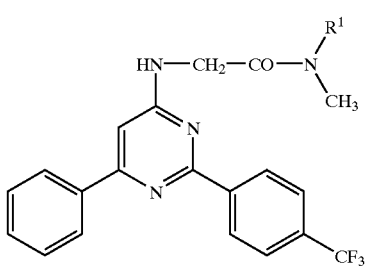

(II)

wherein $R^1$ is the same as defined above.

The chlorinating agent for this process includes N-chlorosuccinamide.

The solvent includes, for example, halogenated hydrocarbons (e.g., chloroform, methylene chloride, etc.), or acidic solvents (e.g., acetic acid, hydrochloric acid, sulfuric acid, etc.). The reaction temperature varies according to the types of the starting compounds and the reaction conditions, but it is usually in the range of about 0° C. to about 150° C., preferably in the range of about 20° C. to about 100° C.

On the other hand, the intermediate (II) may be prepared by the following process.

The intermediate (II) may be prepared by reacting a compound of the formula (III):

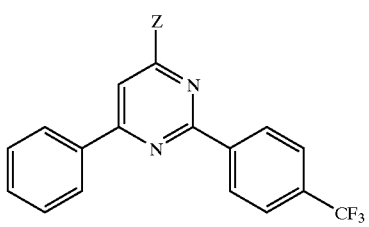

(III)

wherein Z is a leaving atom or a leaving group, with a compound of the formula (IV):

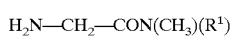

(IV)

wherein $R^1$ is the same as defined above.

The leaving atom or the leaving group represented by Z in the formula (III) includes an atom or a group which may be removed in the form of HZ together with the hydrogen atom of the NH moiety of the compound (IV) under the reaction conditions, for example, a halogen atom (e.g., chlorine, bromine, iodine), a lower alkylsulfonyloxy group (e.g., methanesulfonyloxy), a trihalogenomethanesulfonyloxy group (e.g., trifluoromethanesulfonyloxy), and an arylsulfonyloxy group (e.g., benzenesulfonyloxy, p-toluenesulfonyloxy).

The reaction of the compound (III) and the compound (IV) is carried out under atmospheric pressure or under pressure in a suitable solvent or without a solvent.

The solvent includes, for example, aromatic hydrocarbons (e.g., toluene, xylene), ketones (e.g., methyl ethyl ketone, methyl isobutyl ketone), ethers (e.g., dioxane, diglyme), alcohols (e.g., ethanol, isopropanol, butanol), acetonitrile, dimethylformamide, dimethyl-sulfoxide. The reaction is preferably carried out in the presence of a base. The base includes, for example, alkali metal carbonates (e.g., sodium carbonate, potassium carbonate), alkali metal hydrogen carbonates (e.g., sodium hydrogen carbonate, potassium hydrogen carbonate), and tertiary amines (e.g., triethylamine), but the excess amount of the compound (IV) may be used instead. The reaction temperature varies according to the types of the starting compounds and the reaction conditions, but it is usually in the range of about 40° C. to about 200° C., preferably in the range of about 100° C. to about 170° C.

The starting compound (III) may be prepared, for example, by halogenating or sulfonylating a compound of the formula (V):

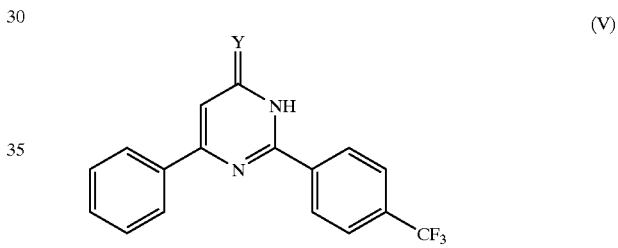

(V)

wherein Y is an oxygen atom or a sulfur atom, in a conventional manner.

The halogenation is carried out, for example, by reacting the compound (V) with a halogenating agent (e.g., phosphorus oxychloride, phosphorus tribromide). The sulfonylation is carried out, for example, by reacting the compound (V) wherein Y is an oxygen atom with a sulfonylating agent (e.g., methanesulfonyl chloride, p-toluenesulfonyl chloride, trifluoromethanesulfonyl chloride, trifluoromethanesulfonic anhydride).

The starting compound (V) may be prepared by a conventional method, for example, by the method disclosed in WO 96/32383 or by a modified method thereof.

Another starting compound (IV) used in the above process may be prepared by a conventional method, for example, by the method disclosed in WO 96/32383, or by a modified method thereof.

The desired compounds obtained in the above processes can be isolated and purified by a conventional method such as chromato-graphy, recrystallization, re-precipitation, etc.

The characteristics of the pharmacological activities of the present compounds are explained by the results of the following pharmacological experiments on the compounds of the present invention.

Experiment 1: Collagen-induced Arthritis Inhibitory Test

Collagen-induced arthritis inhibitory test is an experimental model for rheumatoid arthritis reported by Trethan, D. E.

et al. [cf. J. Exp. Med., 146, 857 (1977)], and thereafter Kakimoto, K. et al. demonstrate that collagen-induced arthritis inhibitory test is useful as an evaluating tool for not only anti-inflammatory agents, but also immuno suppressing agents and immuno modulating agents, based on the mechanism of onset of the disease [cf. J. Immunol., 140, 78–83 (1988)].

Collagen-induced arthritis inhibitory test was carried out according to the method of Kakimoto, K. et al. (cf. above reference of Kakimoto, K. et al.) with slight modification. That is, solubilized bovine cartilage type II collagen (product of Elastine Products, U.S.A.) was emulsified in complete Freund's adjuvant (product of DIFCO Lab., U.S.A.) to give a homogeneous emulsion. Male mice of DBA/IJ strain (6 week-old; product of Nippon Charles River, Japan) were immunized by injection at the base of the tail with 150 μg of the emulsified collagen. Twenty one days after the first immunization, arthritis was induced by a booster immunization of 150 μg of the emulsified collagen prepared in the same manner as above at the base of the tail again. A test compound was orally administered 5 days a week except for Saturdays and Sundays, which was started on the day of the first immunization and continued until the termination of the experiment. Mice were daily observed since the 8th day after the booster immunization for the onset of arthritis, and an arthritic score was derived by grading the severity of involvement of each paw five scales according to the method of Wood, F. D. et al. [cf. Int. Arch. Allergy Appl. Immunol., 35, 456–467 (1969)] with slight modification as shown in Table 1. The severity of arthritis was estimated by the sum of the scores of all 4 paws of both forepaws and both hind paws, and the onset of the disease was considered when score 1 was observed.

TABLE 1

| Score | Symptoms |
| --- | --- |
| 0 | No changes |
| 1 | Erythema and swelling of only one interphalangeal joint in the paws |
| 2 | Erythema and swelling of two or more interphalangeal joints in the paws, or erythema and swelling of a large joint at the wrist or ankle of the paws |
| 3 | Severe erythema and swelling of the entire paws |
| 4 | Reaching the maximum level of swelling of the entire paws |

The inhibitory rate was obtained by comparing the score of arthritis on the 52nd day after the first immunization with that of the control group. The results are shown in Table 2.

Test Compounds

Compound of Example 1: 2-[5-chloro-6-phenyl-2-(4-trifluoromethyl-phenyl)-4-pyrimidinylamino]-N,N-dimethylacetamide Compound of Example 2: 2-[5-chloro-6-phenyl-2-(4-trifluoromethyl-phenyl)-4-pyrimidinylamino]-N-cyclopropyl-N-methylacetamide Compound of Reference Example A: 2-[5,6-dimethyl-2-(4-trifluoro-methylphenyl)-4-pyrimidinylamino]-N,N-dipropylacetamide (the compound of Example 6 disclosed in WO 96/32383)

Compound of Reference Example B: 2-[5,6-dimethyl-2-(4-trifluoro-methylphenyl)-4-pyrimidinylamino]-N,N-dimethylacetamide (the compound of Example 206 disclosed in JP-A-10-130150)

TABLE 2

| Test Comp. | Dose (mg/kg) | Inhibitory rate (%) |
| --- | --- | --- |
| 1* | 10 | 96.0 |
|    | 3  | 72.0 |
|    | 1  | 58.0 |
|    | 0.3 | 20.0 |
| 2* | 10 | 96.6 |
|    | 3  | 85.5 |
|    | 1  | 66.0 |
|    | 0.3 | 29.1 |
| A** | 10 | 73.2 |
|    | 3  | 15.5 |
| B** | 10 | 97.6 |
|    | 3  | 63.9 |
|    | 1  | 41.8 |
|    | 0.3 | 0.0 |

*The compound of Example 1 or Example 2
**The compound of Reference Example A or Reference Example B As is show in Table 2 in above Experiment 1, the compounds of Examples 1 and 2 sowed potent inhibitory effects of more than 70% at a dose of 3 mg/kg and of more than 50% even at a dose of 1 mg/kg in the collagen-induced arthritis inhibitory test, which is a model for immuno inflamatory diseases such as rheumatoid arthritis. On the other hard, the compound of Reference Example A hardly showed any inhibitory effects at a dose of 3 mg/kg, and there were recognized significant differences between the compound of Reference Example A and the compound of Example 1 and Example 2. In addition, the compound of Reference Example B showed an anti-rheumatoid activity as potent as the compounds of Example 1 and Example 2 at a dose of 10 mg/kg, but the activity thereof at a dose of 3 mg/kg or less was weaker than the compounds of Example 1 and Example 2.

Experiment 2: Subacute Toxicity Test

Subacute toxicity test was carried out by repetitive administration of a test compound to mice for 14 days. That is, a test compound was orally administered to male mice of ICR strain once a day for 14 days. On the day following the final administration, the mice were anesthetized with Nembutal, and the blood was taken out therefrom, and further various organs were taken out. The wet-weight of each organ was determined, and was converted into a weight per body, and then compared. The blood plasma was subjected to various biochemical tests, mainly to tests for parameters for liver function and renal function. The results of these tests were statistically compared with those in the solvent-treated control group. The data of the biochemical tests, for example, ALT (alanine aminotransferase) as a parameter for liver dysfunction and other remarks observed during the test (see the column of "other remarks" in Table 3) are shown in Table 3.

TABLE 3

| Test Compound | ALT (Dose, mg/kg) | | | Other remarks |
| --- | --- | --- | --- | --- |
|  | 100 | 200 | 300 |  |
| 1* | – | – | – | no particular remark |
| 2* | – | – | – | no particular remark |

TABLE 3-continued

| Test Compound | ALT (Dose, mg/kg) | | | Other remarks |
|---|---|---|---|---|
| | 100 | 200 | 300 | |
| A** | − | − | + | no particular remark |
| B** | ++ | | | peritoneal fluid, renal damage |

*The compound of Example 1 or Example 2
**The compound of Reference Example A or Reference Example B
−no significant differences (Student's t-test)
+$p < 0.05$ (Student's t-test)
++$p < 0.01$ (Student's t-test)

The above test was carried out on the compounds of Example 1 and Example 2, and as well as on the compounds of Reference Example A and Reference Example B. In the group treated with the compounds of Example 1 and Example 2, it was found that the change in the body weight during the test, i.e., from the beginning of the administration to the termination of the administration, was not significantly different from that of the vehicle-treated control group even at a high dose of 300 mg/kg. In addition, the wet-weights of various organs such as liver, spleen were not significantly different from those in the vehicle-treated control group either. Besides, the data of the biochemical tests, for example, ALT (alanine aminotransferase) and AST (aspartate amino-tranferase) which are used as parameters for liver dysfunction and BUN (blood urea nitrogen) as a parameter for renal dysfunction, were also not significantly different from those in the vehicle-treated control group. Thus, it was confirmed that the compounds of Examples 1 and 2 show very high safety.

On the other hand, the compound of Reference Example A did not affect on the above parameters at a dose of 100 mg/kg, but at a high dose of 300 mg/kg, it did affect the liver in some degree, and hence, the compound of Reference Example A shows lower safety than the compounds of Example 1 and Example 2 do. Further, the compound of Reference Example B, which shows a potent anti-rheumatoid activity, showed a potent side effect on liver and kidney even at a dose of 100 mg/kg, and hence, the compound of Reference Example B shows apparently lower safety than the compounds of Example 1 and Example 2.

As is clear from the results of the above pharmacological tests, the compounds (I) of the present invention exhibit an excellent anti-rheumatoid activity in vivo, and show low toxicity, and hence, the present compounds are useful as an agent in the prophylaxis or treatment of immuno inflammatory diseases such as rheumatoid diseases (e.g., rheumatoid arthritis, Behcet disease, ankylosing spondylitis, etc.) and autoimmune diseases (e.g., multiple sclerosis, systemic lupus erythematosus, Sjögren syndrome, etc.). Especially the compound of Example 2 shows a quite potent anti-rheumatoid activity and hence especially useful.

The compounds of the present invention can be administered either orally, parenterally or rectally. The dose of the compounds of the present invention varies according to the types of the compound, the administration routes, the conditions, ages of the patients, etc., but it is usually in the range of 0.1–10 mg/kg/day, preferably in the range of 0.3–5 mg/kg/day.

The compounds of the present invention are usually administered in the form of a pharmaceutical preparation, which is prepared by mixing thereof with a pharmaceutically acceptable carrier or diluent. The pharmaceutically acceptable carrier or diluent may be any conventional ones being usually used in the pharmaceutical field, and do not react with the compounds of the present invention. Suitable examples of the pharmaceutically acceptable carrier or diluent are lactose, inositol, glucose, mannitol, dextran, cyclodextrin, sorbitol, starch, partly pregelatinized starch, white sugar, magnesium metasilicate aluminate, synthetic aluminum silicate, crystalline cellulose, sodium carboxymethylcellulose, hydroxypropyl starch, calcium carboxylmethylcellulose, ion exchange resin, methylcellulose, gelatin, gum arabic, hydroxypropylcellulose, low substituted hydroxypropylcellulose, hydroxypropylmethylcellulose, polyvinylpyrrolidone, polyvinyl alcohol, alginic acid, sodium alginate, light anhydrous silicic acid, magnesium stearate, talc, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, propyleneglycol, water, ethanol, polyoxyethylene-hydrogenated caster oil (HCO), sodium chloride, sodium hydroxide, hydrochloric acid, disodium hydrogen phosphate, sodium dihydrogen phosphate, citric acid, glutamic acid, benzyl alcohol, methyl p-hydroxybenzoate, ethyl p-hydroxybenzoate, etc.

The pharmaceutical preparation is, for example, tablets, capsules, granules, powders, syrups, suspensions, suppositories, injection preparations, etc. These preparations may be prepared by a conventional method. In the preparation of liquid preparations, the compound of the present invention may be dissolved or suspended in water or a suitable other solvent, when administered. Tablets and granules may be coated by a conventional method. In the injection preparations, it is preferable to dissolve the compound of the present invention in water, but if necessary, it may be dissolved by using an isotonic agent or a solubilizer, and further, a pH adjuster, a buffering agent or a preservative may be added thereto.

These preparations may contain the compound of the present invention at a ratio of at least 0.01%, preferably at a ratio of 0.1–70%. These preparations may also contain other therapeutically effective compounds as well.

BEST MODE FOR CARRYING OUT THE INVENTION

The present invention is illustrated in more detail by the following Reference Examples and Examples, but should not be construed to be limited thereto.

The identification of the compounds is carried out by Elementary analysis, Mass spectrum, IR spectrum, NMR spectrum, etc.

REFERENCE EXAMPLE 1

Preparation of 6-phenyl-2-(4-trifluoronethylphenyl)-4 (3H)-pyrimidinone:

To a mixture of a 28% solution of sodium methoxide in methanol (15 g) and anhydrous ethanol (50 ml) is added 4-trifluoro-methylbenzamidine hydrochloride dihydrate (14.9 g) at room temperature. The mixture is stirred at room temperature for 30 minutes, and thereto is added dropwise ethyl benzoylacetate (10 g) at the same temperature. After the addition, the mixture is heated under reflux for 8 hours. The reaction mixture is concentrated under reduced pressure, and the residue is dissolved in water. The pH value of the solution thus obtained is adjusted to pH 4 with conc. hydrochloric acid at 0–5° C. under stirring. The precipitates are collected by filtration, washed with water, and washed with ethanol to give the desired compound (10 g).

M.p. >300° C.

REFERENCE EXAMPLES 2

Preparation of 4-chloro-6-phenyl-2-(4-trifluoromethylphenyl)pyrimidine:

A mixture of 6-phenyl-2-(4-trifluoromethylphenyl)-4-(3H)-pyrimidinone (10 g) and phosphorus oxychloride (7.3 g) was stirred at 80° C. for 3 hours. To the reaction mixture is added water, and the mixture is neutralized with an aqueous sodium hydroxide solution (1 mol/L). The precipitates are collected by filtration, washed with water, and recrystallized from isopropyl alcohol to give the desired compound (9.5 g).

M.p. 82–84° C.

Example A and Example B as described below illustrate the preparation of the intermediate (II), and Example 1 and Example 2 illustrate the preparation of the desired compound of the present invention.

EXAMPLE A

Preparation of N,N-dimethyl-2-[6-phenyl-2-(4-trifluoromethylphenyl)-4-pyrimidinylamino]acetamide:

A mixture of 4-chloro-6-phenyl-2-(4-trifluoromethylphenyl)-pyrimidine (15 g), 2-amino-N,N-dimethylacetamide (8.2 g) and triethyl-amine (5.4 g) is heated at 150° C. under reflux for 2 hours. To the reaction mixture are added water and chloroform, and the chloroform layer is separated, dried over anhydrous sodium sulfate, and concentrated under reduced pressure. The residue is purified by silica gel column chromatography (eluent: chloroform), and recrystallized from ethanol to give the desired compound (16 g).

M.p. 178–179° C.

EXAMPLE B

Preparation of N-cyclopropyl-N-methyl-2-[6-phenyl-2-(4-trifluoromethyl-phenyl)-4-pyrimidinylamino]acetamide:

A mixture of 4-chloro-6-phenyl-2-(4-trifluoromethylphenyl)-pyrimidine (15 g), 2-amino-N-cyclopropyl-N-methylacetamide (10 g) and triethylamine (5.4 g) is heated at 150° C. under reflux for 2 hours. To the reaction mixture are added water and chloroform, and the chloroform layer is separated, dried over anhydrous sodium sulfate, and concentrated under reduced pressure. The residue is purified by silica gel column chromatography (eluent: chloroform), and recrystallized from ethanol to give the desired compound (17 g).

M.p. 179–180° C.

EXAMPLE 1

Preparation of 2-[5-chloro-6-phenyl-2-(4-trifluoromethylphenyl)-4-pyrimidinylamino]-N,N-dimethylacetamide:

A mixture of N,N-dimethyl-2-[6-phenyl-2-(4-trifluoromethyl-phenyl)-4-pyrimidinylamino]acetamide (15.9 g), N-chlorosuccinimide (6.4 g) and acetic acid (80 ml) is stirred at 90° C. for 1.5 hour. The reaction mixture is concentrated under reduced pressure, and water and chloroform are added to the residue. The mixture is neutralized with an aqueous sodium hydroxide solution (1 mol/L), and the chloroform layer is separated. The chloroform layer is dried over anhydrous sodium sulfate, concentrated under reduced pressure, and the residue is purified by silica gel column chromatography (eluent: chloroform), and recrystallized from ethanol to give the desired compound (16 g).

M.p. 183–184° C.

EXAMPLE 2

Preparation of 2-[5-chloro-6-phenyl-2-(4-trifluoromethylphenyl)-4-pyrimidinylamino]-N-cyclopropyl-N-methylacetamide:

N-Cyclopropyl-N-methyl-2-[6-phenyl-2-(4-trifluoromethyl-phenyl)-4-pyrimidinylamino]acetamide and N-chlorosuccinimide are treated in the same manner as in Example 1, and the resultant is recrystallized from ethanol to give the desired compound.

M.p. 188–189° C.

Preparation 1: Preparation of Tablets

| | |
|---|---|
| 2-[5-Chloro-6-phenyl-2-(4-trifluoromethylphenyl)-4-pyrimidinylamino]-N,N-dimethylacetamide | 20 g |
| Lactose | 75 g |
| Corn starch | 20 g |
| Crystalline cellulose | 25 g |
| Hydroxypropylcellulose | 3 g |

The above components are mixed and kneaded in a conventional manner, and the mixture is granulated. To the mixture are added light anhydrous silicic acid (0.7 g) and magnesium stearate (1.3 g), and the mixture is further tabletted to give 1,000 tablets (each 145 mg).

Preparation 2: Preparation of Capsules

| | |
|---|---|
| 2-[5-Chloro-6-phenyl-2-(4-trifluoromethylphenyl)-4-pyrimidinylamino]-N-cyclopropyl-N-methylacetamide | 40 g |
| Lactose | 127 g |
| Corn starch | 25 g |
| Hydroxypropylcellulose | 3.5 g |
| Light anhydrous silicic acid | 1.8 g |
| Magnesium stearate | 2.7 g |

The above components are mixed and kneaded in a conventional manner, and the mixture is granulated, and each 200 mg of the granule is packed into a capsule to give 1,000 capsules.

Preparation 3: Preparation of Powder

| | |
|---|---|
| 2-[5-Chloro-6-phenyl-2-(4-trifluoromethylphenyl)-4-pyrimidinylamino]-N-cyclopropyl-N-methylacetamide | 150 g |
| Lactose | 820 g |
| Hydroxypropylcellulose | 25 g |
| Light anhydrous silicic acid | 5 g |

The above components are mixed by a conventional manner to give a powder preparation.

INDUSTRIAL APPLICABILITY

The compounds (I) of the present invention show a potent anti-rheumatoid activity in vivo and low toxicity, and hence, they are useful in the prophylaxis or treatment of various immuno inflammatory diseases such as rheumatoid diseases (e.g., rheumatoid arthritis, Behcet disease, ankylosing spondylitis, etc.) and autoimmune inflammatory diseases (e.g., multiple sclerosis, systemic lupus erythematosus, Sjögren syndrome, etc.). In addition, the compound (II) of the present invention is useful as an intermediate for preparing the compound (I) of the present invention.

What is claimed is:

1. A [5-chloro-6-phenyl-2-(4-trifluoromethylphenyl)-4-pyrimidinyl-amino]acetamide derivative of the formula (I):

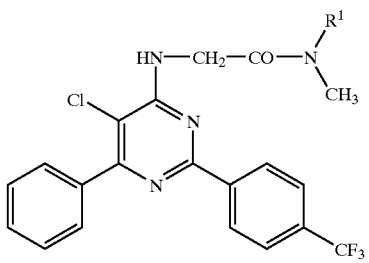

(I)

wherein $R^1$ is a methyl group or a cyclopropyl group.

2. 2-[5-Chloro-6-phenyl-2-(4-trifluoromethylphenyl)-4-pyrimidinyl-amino]-N,N-dimethylacetamide.

3. 2-[5-Chloro-6-phenyl-2-(4-trifluoromethylphenyl)-4-pyrimidinyl-amino]-N-cyclopropyl-N-methylacetamide.

4. A process for preparing a [5-chloro-6-phenyl-2-(4-trifluoro-methylphenyl)-4-pyrimidinylamino]acetamide derivative of the formula (I):

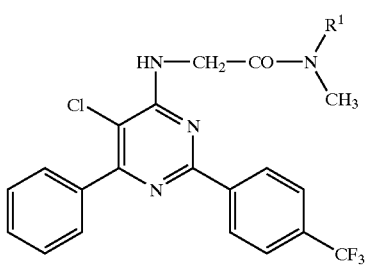

(I)

wherein $R^1$ is a methyl group or a cyclopropyl group, which comprises chlorinating a compound of the formula (II):

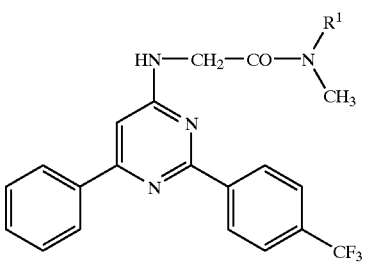

(II)

wherein $R^1$ is the same as defined above.

5. A pharmaceutical composition comprising one or more compounds selected from claim 1 and a pharmaceutically acceptable carrier or diluent.

6. A method for treatment of an immuno inflammatory disease, which comprises administering an effective amount of a compound as set forth in claim 1, to a patient suffering from an immuno inflammatory disease.

7. A [6-phenyl-2-(4-trifluoromethylphenyl)-4-pyrimidinylamino]-acetamide derivative of the formula (II):

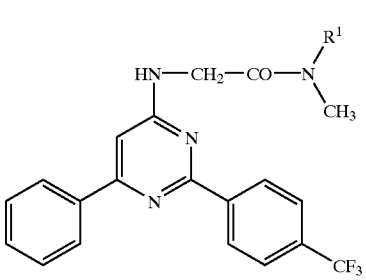

(II)

wherein $R^1$ is a methyl group or a cyclopropyl group.

8. A pharmaceutical composition comprising one or more compounds selected from claim 2 and a pharmaceutically acceptable carrier or diluent.

9. A pharmaceutical composition comprising one or more compounds selected from claim 3 and a pharmaceutically acceptable carrier or diluent.

10. A method for treatment of an immuno inflammatory disease, which comprises administering an effective amount of a compound as set forth in claim 2, to a patient suffering from an immuno inflammatory disease.

11. A method for treatment of an immuno inflammatory disease, which comprises administering an effective amount of a compound as set forth in claim 3, to a patient suffering from an immuno inflammatory disease.

* * * * *